(12) United States Patent
Kaercher et al.

(10) Patent No.: US 10,342,560 B2
(45) Date of Patent: Jul. 9, 2019

(54) MEDICAL INSTRUMENT

(71) Applicant: KARL STORZ GmbH & Co. KG, Tuttlingen (DE)

(72) Inventors: Daniel Kaercher, Radolfzell (DE); Jochen Stefan, Wald (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 301 days.

(21) Appl. No.: 15/441,384

(22) Filed: Feb. 24, 2017

(65) Prior Publication Data
US 2017/0252053 A1 Sep. 7, 2017

(30) Foreign Application Priority Data
Mar. 1, 2016 (DE) .................. 10 2016 103 640

(51) Int. Cl.
*A61B 17/29* (2006.01)
*A61B 17/062* (2006.01)

(52) U.S. Cl.
CPC .......... *A61B 17/29* (2013.01); *A61B 17/062* (2013.01); *A61B 17/2909* (2013.01); *A61B 2017/292* (2013.01); *A61B 2017/2902* (2013.01); *A61B 2017/2926* (2013.01); *A61B 2017/2946* (2013.01)

(58) Field of Classification Search
CPC .......... A61B 17/062; A61B 17/29; A61B 2017/2902; A61B 2017/2926; A61B 2017/2932; A61B 2017/2933; A61B 2017/2936; A61B 2017/2939; A61B 2017/294; A61B 2017/2946
See application file for complete search history.

(56) References Cited

U.S. PATENT DOCUMENTS

| | | | |
|---|---|---|---|
| 5,626,607 A | 5/1997 | Malecki et al. | |
| 6,368,340 B2* | 4/2002 | Malecki | A61B 17/00234 |
| | | | 606/204 |
| 7,896,900 B2 | 3/2011 | Frank et al. | |
| 8,882,799 B2 | 11/2014 | Frank | |
| 2001/0016750 A1 | 8/2001 | Malecki et al. | |
| 2012/0232580 A1 | 9/2012 | Aue | |
| 2013/0053835 A1* | 2/2013 | Bacher | A61B 17/29 |
| | | | 606/1 |
| 2017/0252053 A1* | 9/2017 | Kaercher | A61B 17/29 |

FOREIGN PATENT DOCUMENTS

DE 10 2009 055 747 A1 6/2011
EP 2 522 280 A1 11/2012

* cited by examiner

*Primary Examiner* — Ryan J. Severson
(74) *Attorney, Agent, or Firm* — Muncy, Geissler, Olds & Lowe, P.C.

(57) ABSTRACT

A medical instrument according to the invention has an elongate shank, and a tool which is arranged on a distal end portion of the shank and which comprises two tool elements interacting with each other, of which at least one tool element is movable by a longitudinally displaceable first transmission element. A distal end portion of the first transmission element has a surface inclined with respect to a direction of displacement, and the distal end portion of the shank, or an element connected non-displaceably thereto, has a mating surface which is inclined with respect to the direction of displacement and which, with the inclined surface, forms an interspace dependent on a displacement of the distal end portion of the first transmission element.

14 Claims, 4 Drawing Sheets

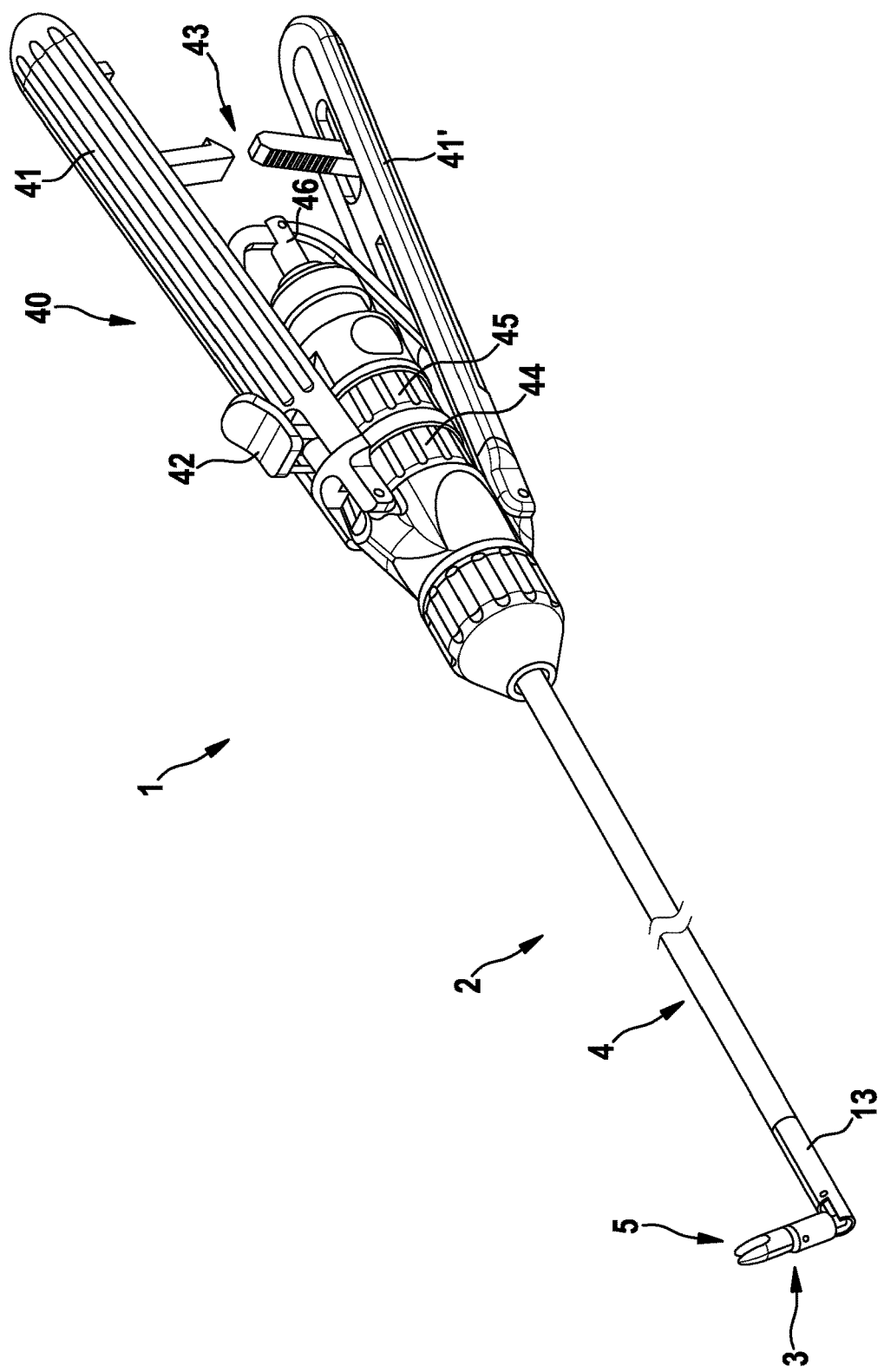

MEDICAL INSTRUMENT

This nonprovisional application claims priority under 35 U.S.C. § 119(a) to German Patent Application No. 10 2016 103 640.4, which was filed in Germany on Mar. 1, 2016, and which is herein incorporated by reference.

BACKGROUND OF THE INVENTION

Field of the Invention

The present invention relates to a medical instrument, in particular a surgical instrument, with an elongate shank, and a tool which is arranged on a distal end portion of the shank and which comprises two tool elements interacting with each other, in particular for the purpose of holding an object, of which at least one tool element is movable by means of a longitudinally displaceable first transmission element.

Description of the Background Art

In medical instruments of this kind, it is often necessary that an object should be grasped and held firmly with the tool in order to be able to move the object by means of the surgical instrument and, for example, perform surgical manipulations using the object. For example, a surgical needle should be grasped and held as firmly as possible in order to insert the needle into tissue. For this purpose, it is desirable for the interacting tool elements to be blocked or locked in a holding position in which the surgical element is grasped, such that a user does not have to apply any more force in order to continue holding the object and is able to move the latter comfortably. Locking of this kind can be obtained, for example, by means of a catch which is arranged on a handle and with which a grip, with which the at least one movable tool element can be actuated via a pull rod, can be locked in a holding position. In this way, the object can be held securely and firmly without the user having to continue applying force for this purpose. However, the pull rod is in this case tensioned, which is disadvantageous in terms of the handling and durability of the instrument. Moreover, in the case where the tool is mounted rotatably about a longitudinal axis, the rotary bearing of the tool is tensioned in the locked state and can be rotated only by application of considerable force. The high degree of loading during rotation can also cause damage to the instrument.

DE 10 2009 055 747 A1 discloses surgical forceps in which a relative movement of the jaw parts of the forceps mouth is controlled via the engagement of at least one cam on the forceps mouth or on an actuating rod, in a groove arranged on the actuating rod or on the forceps mouth, the groove being inclined with respect to the direction of displacement of the actuating rod. The groove is provided, in at least some regions, with an angle of inclination which is smaller than the angle of inclination up to which self-retention in the groove occurs. The self-retention ensures that, after an object has been clamped in the forceps mouth by actuation of the actuating rod, the clamped position is maintained, even if the actuating rod is let go.

EP 2 522 280 A1 discloses a medical instrument, in particular a surgical needle holder, comprising two jaw parts, wherein at least one of the jaw parts is pivotable relative to the other one between a grasping state for grasping the object and a release state for releasing the object. The instrument has a latching mechanism for blocking the at least one pivotable jaw part in the grasping state, wherein a connection pin, connecting the pivotable jaw part to a latching element, is received in an elongate opening of the latching element. The elongate opening is divided into several segments by periodical projections, such that the pivotable jaw part is pivotable stepwise from one stable and locked position to another stable and locked position.

According to U.S. Pat. No. 7,896,900 B2, a medical instrument, in particular a surgical needle holder, is provided with a latching mechanism for immobilizing at least one pivotable jaw part in a grasping state for the purpose of grasping an object, wherein the latching mechanism comprises a latching element formed by an elastically deformable and, for example, C-shaped lever. By axial movement of a force transmission element, the lever is caused to snap-fit into a locked and stable state.

In the abovementioned solutions, the jaw parts are locked or immobilized in a holding position, the latching mechanism being arranged in the distal area of the instrument. However, it has been found that a sufficient holding force, in particular for holding a surgical needle, cannot always be achieved in this way, and/or that a relatively high force has to be applied for locking and unlocking.

SUMMARY OF THE INVENTION

It is an aim of the present invention to specify a medical instrument which is of the type in question and in which the abovementioned disadvantages are avoided as far as possible.

A medical instrument according to the invention is designed in particular as a surgical instrument, preferably as an endoscopic instrument, and has an elongate shank designed for insertion into a cavity inside the body. The shank is preferably rigid at least in some areas, but can also be flexible in some areas. A tool, which serves in particular for performing surgical manipulations in an endoscopic intervention, is arranged on the distal end portion of the shank (i.e. the end remote from the user). The tool is preferably arranged on the distal end of the distal end portion of the shank and is preferably designed in such a way that, at least in a closed position at the tip of the shank, it can be inserted with the latter through a body opening into the cavity inside the body. The tool comprises two interacting tool elements which are designed in particular for the purpose of grasping and holding an object and are movable toward each other. The medical instrument can be designed as a needle holder, for example, in which case the tool elements are adapted for grasping and holding a surgical needle.

At least one of the two tool elements, which is designated hereinbelow as a movable tool element, is arranged so as to be movable relative to the distal end portion of the shank in order to interact with the other tool element, and it is movable from the direction of the proximal end of the shank (i.e. the end near the user) by means of a first transmission element. The first transmission element can be designed, for example, as a pull rod or push rod and can extend in some areas inside or on an outer face of the shank. To move the at least one movable tool element, the first transmission element is mounted in a longitudinally displaceable manner in or on the shank. In order to actuate the at least one movable tool element, a manually activatable grip can be provided at the proximal end of the shank, said grip being coupled to the proximal end of the first transmission element. However, motorized actuation of the first transmission element can also be provided.

In particular, the tool can comprise a movable tool element and a stationary tool element, in which case the movable tool element is movable toward the stationary one in order to grasp and hold the object and can be moved away from the stationary one again in order to release the object. The movable tool element can be mounted pivotably on a main part of the tool and, for example, can be designed as a jaw part which is pivotable with respect to a stationary jaw part connected rigidly to the main part. However, the tool can also, for example, comprise two tool elements movable toward one another, for example two jaw parts which are mounted pivotably on the main part of the tool and which can be pivoted toward each other in order to grasp and hold the object and can be pivoted away from each other in order to release the object. If two pivotable jaw parts are provided, they can be mounted pivotably on a common axis, for example. The first transmission element can be coupled to the pivotable jaw part or the pivotable jaw parts in a manner known per se, such that a pivoting movement of the jaw part or of the jaw parts can be brought about by a longitudinal displacement of the first transmission element.

According to the invention, a distal end portion of the first transmission element has a surface inclined with respect to a direction of displacement of the distal end portion of the first transmission element. The direction of displacement is in particular parallel, or approximately parallel, to a longitudinal axis of the distal end portion of the shank. Moreover, the distal end portion of the shank, or an element connected non-displaceably thereto, has a mating surface which is likewise inclined with respect to the direction of displacement of the distal end portion of the first transmission element. The mating surface can be arranged, for example, on an outer tube of the distal end portion of the shank, or on an element of the distal end portion of the shank that is not axially displaceable with respect to the outer tube; said element can be fixedly connected, for example, to the main part of the tool. Both the surface and the mating surface, which are also referred to hereinbelow as inclined or oblique surfaces, rise in particular in the proximal direction or in the distal direction, wherein the inclination or gradient of the inclined surfaces is in each case considered parallel to the direction of displacement, for example along the longitudinal axis of the distal end portion of the shank. The mating surface, along with the inclined surface of the distal end portion of the first transmission element, forms an interspace dependent on a displacement position of the distal end portion of the first transmission element relative to the distal end portion of the shank. In particular, the inclined surface of the distal end portion of the first transmission element and the mating surface can be arranged lying opposite each other at least in one displacement position or in a subregion of a displacement path of the distal end portion of the first transmission element. One or more oblique surfaces and/or mating surfaces can be provided, which can be assigned to each other in such a way that one or more interspaces are formed.

The medical instrument according to the invention moreover comprises at least one locking element which is movable into the interspace in such a way that a longitudinal displacement of the distal end portion of the first transmission element relative to the distal end portion of the shank can be blocked and, in this way, the at least one movable tool element can be locked. To release the blocking, or to permit unlocking, the at least one locking element is movable back out of the interspace. The locking element does not have to be introduced completely into the interspace and it also does not have to be completely removed therefrom, and instead a movement directed into the interspace and a movement directed out of the latter can be sufficient for blocking and unblocking. In particular, the at least one locking element is movable into the interspace to such an extent that, by contact with the oblique surface and the mating surface, it blocks a movement of the first transmission element relative to the distal end portion of the shank at least in one direction of movement and is held in the interspace preferably by frictional engagement. Accordingly, the at least one locking element is movable in the opposite direction to such an extent that the frictional engagement with at least one of the oblique surfaces forming the interspace is canceled and the distal end portion of the first transmission element is again movable relative to the distal end portion of the shank. The corresponding movement of the at least one locking element can be controlled from the direction of the proximal end of the shank by means of a second transmission element. The second transmission element can be displaceable in particular in a longitudinal direction of the shank and can be guided substantially parallel to the first transmission element, for example in some areas on an outer side of the shank or inside the shank, and can be designed at least in part as a pull rod or push rod. It is possible for several locking elements to be provided, which are movable into and out of one or more interspaces in the described manner.

Since the distal end portion of the first transmission element and the distal end portion of the shank have oblique surfaces which lie opposite each other at least in one displacement position of the distal end portion of the first transmission element, an interspace is formed whose width changes during a longitudinal displacement of the first transmission element relative to the distal end portion of the shank. According to the invention, the interspace is used for introduction of a locking element in order to block the first transmission element relative to the distal end portion of the shank and thereby to lock the at least one movable tool element in a holding position in which an object can be held between the tool elements. The tool can thus be locked in a simple and safe way, as a result of which an object such as a surgical needle can be held securely between the two tool elements, without further force having to be applied by the user. It is also possible in this way to obtain simple and safe unlocking in order to release the held object, the user having to apply only a relatively slight force for the unlocking.

According to a preferred embodiment of the invention, the oblique surface of the distal end portion of the first transmission element is arranged on an outer side of the distal end portion of the first transmission element, and the mating surface is arranged on an inner side of a tubular element. The tubular element can be, for example, an outer tube of the distal end portion of the shank, or the tubular element can be the element connected non-displaceably to the distal end portion of the shank. In particular, the mating surface can be arranged on an inner side of a tubular or sleeve-shaped element which is inserted in a rotatable but axially fixed manner into the outer tube; the element can, for example, be connected fixedly to the main part of the tool. In this way, an arrangement is created which has a simple structure and is particularly stable and able to support loads.

The tool is preferably designed in such a way that, by means of a displacement of the first transmission element in the proximal direction, the two tool elements can be closed in order to grasp an object, and, consequently, the object can be held by a tensile stress acting inside the first transmission element. The oblique surface and the mating surface are both designed rising radially in the proximal direction, that is to say, viewed in an axial section for example, with the radial distance from a longitudinal axis of the distal end portion of the first transmission element increasing in the proximal direction. In this embodiment, the at least one movable tool element can be subjected to a holding force for firmly holding the object by generating a tensile stress in the first transmission element, the movable tool element can be locked in this holding position by moving the at least one locking element, and the holding force can be maintained by the tensile stress between the distal end portion of the first transmission element and the movable tool element. This allows a particularly strong holding force to be applied and thus permits a particularly firm and secure hold of the grasped object.

Alternatively, provision can be made, for example, that the tool elements can be closed by a displacement of the first transmission element in a distal direction, in which case both oblique surfaces are designed rising radially in the distal direction. Here, the holding force can be maintained by a shearing stress between the movable tool element and the distal end portion of the first transmission element.

Particularly preferably, the surface and the mating surface both form an interspace that is wedge-shaped when viewed in an axial section. If the tool elements are closeable by displacement of the first transmission element in the proximal direction and if the two oblique surfaces rise radially in the proximal direction, the wedge-shaped interspace preferably tapers to a point in the distal direction and is opened out in the proximal direction. By virtue of the fact that the interspace is wedge-shaped, it is possible to block the distal end portion of the first transmission element in a plurality of displacement positions and therefore to lock the at least one movable jaw part in a plurality of positions. This allows objects of different dimensions to be held, for example surgical needles with different diameters, and permits compensation of tolerances. In this way, moreover, the at least one locking element can be moved in and out of the interspace with only slight force being applied, thereby permitting particularly simple locking and unlocking.

Preferably, the oblique surface of the distal end portion of the first transmission element and the mating surface are inclined with respect to the direction of displacement by such angles of inclination that the displacement of the first transmission element can be blocked in a self-retaining manner when the locking element is inserted into the interspace. For example, the oblique surface of the distal end portion of the first transmission element forms an angle in the range of approximately 5° to 6°, for example, to the direction of displacement of the distal end portion of the first transmission element, which direction is at least approximately parallel to the longitudinal axis of the distal end portion of the shank, and the mating surface provided on the distal end portion of the shank forms an angle of approximately 10° to 12°, for example, to the direction of displacement. In this way, the movement of the first transmission element relative to the distal end portion of the shank can be blocked in a self-retaining manner, and, in particular, the at least one movable tool element can be locked in both directions, i.e. both against opening and also against further closing of the tool elements.

Preferably, the at least one locking element is approximately wedge-shaped when viewed in an axial section. In particular, if the two oblique surfaces rise radially in the proximal direction, the locking element has a wedge shape tapering to a point in the distal direction. This likewise allows objects of different sizes to be held and permits compensation of tolerances and a particularly simple insertion and removal of the locking element into and out of the interspace.

Particularly preferably, both the interspace and the locking element are wedge-shaped in an axial section, the wedge angle of the locking element and of the interspace being substantially equal. In this way, it is possible to achieve greater reliability of the locking in a self-retaining manner and, at the same time, locking can be obtained in a greater range of the longitudinal displacement of the first transmission element and therefore in a greater range of positions of the at least one movable tool element or opening widths of the tool. This permits particularly secure holding of needles of different diameter, for example, and improved compensation of tolerances.

It is moreover preferable that the at least one locking element is connected radially movably to a distal end portion of the second transmission element. The distal end portion of the second transmission element is in particular designed as a locking carriage, which is displaceable parallel to the direction of displacement of the distal end portion of the first transmission element and therefore at least approximately parallel to the longitudinal axis of the distal end portion of the shank. The locking element can be displaceable in the radial direction, for example, or can be connected to the locking carriage so as to be pivotable about a transverse axis. This permits simple adaptation of the locking element to different locking positions and, therefore, allows the at least one movable tool element to be locked simply and safely in different positions.

At the proximal end, the at least one locking element preferably carries two mutually opposite lugs which are oriented transversely with respect to the longitudinal direction of the distal end portion of the shank, or transversely with respect to the direction of displacement of the locking carriage, with which lugs it is articulated on the locking carriage or suspended in corresponding recesses of the locking carriage. This permits in a particularly simple manner a radial mobility of the at least one locking element for adaptation to different locking positions.

The at least one locking element is advantageously guided in a groove in the distal end portion of the shank, and the bottom of the groove forms the mating surface. In particular, the distal end portion of the shank can be tubular, in which case the groove is formed on an inner side of the tube or on an inner side of a tubular or sleeve-shaped element inserted into the tube, said groove extending in the direction of displacement or in the longitudinal direction of the distal end portion of the shank, although the bottom of the groove is inclined obliquely with respect to this direction. This allows the at least one movable tool element to be locked in a particularly simple and stable manner.

Two locking elements are preferably present in the distal end portion of the shank, which two locking elements are movable jointly in order to lock and unlock the at least one movable tool element, in particular movable jointly by means of the second transmission element, and can be moved in and out of one or two corresponding interspaces. Particularly secure locking is permitted in a simple manner in this way.

The oblique surface and/or the mating surface can be designed approximately, or in some regions, as plane or conical, or also as convex or hollow in axial section. According to a preferred embodiment, both the oblique surface of the distal end portion of the first transmission element and also the associated mating surface of the distal end portion of the shank are approximately conical, the respective axis of the cone being oriented at least approximately parallel to the direction of displacement of the distal end portion of the first transmission element or to the longitudinal axis of the distal end portion of the shank. In this case, two locking elements can be provided, which can be arranged more or less symmetrically on sides lying opposite each other with respect to the longitudinal axis.

According to another preferred embodiment of the invention, the distal end portion of the first transmission element has two approximately plane, oblique surfaces lying axially opposite each other, and the distal end portion of the shank has two corresponding approximately plane mating surfaces arranged on sides lying opposite each other. In this case, two locking elements are provided which are arranged lying axially opposite each other and which, for locking and unlocking respectively, can be moved into and back out of the two interspaces formed by the respective inclined surfaces lying opposite each other.

According to a particularly preferred embodiment of the invention, the tool is rotatable, relative to the distal end portion of the shank, about a rotation axis which coincides with or is parallel to the longitudinal axis of the distal end portion of the shank. For example, the tool can be rotatable with respect to an outer tube of the distal end portion of the shank. Moreover, in this embodiment, the distal end portion of the first transmission element is likewise designed to be rotatable about the rotation axis, or about an axis parallel thereto, relative to a proximal portion of the first transmission element. For this purpose, the distal end portion of the shank can have a corresponding rotary bearing at the distal end, and the distal end portion of the first transmission element can have a rotary bearing at the proximal end. Moreover, a distal end portion of the second transmission element can be designed as a longitudinally displaceable locking carriage, which is connected to a proximal portion of the second transmission element via an intermediate piece which is rotatable, relative to the locking carriage, about the rotation axis or about an axis parallel thereto. The rotation of the tool, together with the distal end portion of the first transmission element, relative to the other portions of the shank or of the first transmission element can be controlled, for example, by a rotatable shaft which extends inside the shank and which is connected to a main part of the tool for conjoint rotation therewith. By virtue of the fact that the tool is rotatable about a rotation axis parallel to the longitudinal axis of the distal end portion of the shank, the usability of the medical instrument for a large number of situations can be improved. In particular, this means that the tool elements, and an object possibly held by them, can be oriented in a desired direction without having to rotate the proximal portion of the shank. By virtue of the fact that a locking of the at least one movable tool element in a holding position for holding the object takes place inside the distal end portion of the shank, it is possible to relieve the rotary bearings of the tool, and of the distal end portion of the first transmission element, of the holding force. This can make it easier for a user to perform the rotation, and excess wear of the instrument can be avoided.

According to a preferred embodiment of the invention, the distal end portion of the shank is pivotable, relative to a proximal portion of the shank, about a transverse axis directed transversely with respect to the longitudinal axis of the shank. The pivoting movement can be controlled from the direction of the proximal end of the shank, for example by a third transmission element which extends in or on the proximal portion of the shank. Particularly preferably, the distal end portion of the shank is pivotable relative to the proximal portion of the shank about the transverse axis and also the tool is rotatable about a rotation axis directed parallel to the longitudinal axis of the distal end portion of the shank. In this case, provision can be made that the rotatable shaft, which serves to transmit the rotation movement of the tool, is interrupted in the area of a pivot joint serving to angle the distal end portion of the shank, and a rotation is transmitted by means of a toothing, for example, via which a proximal portion of the shaft interacts with a distal portion for transmitting the rotation. Moreover, provision can be made that the distal end portion of the first transmission element is connected to a proximal portion of the first transmission element via an intermediate piece, mounted rotatably relative to the distal end portion of the first transmission element, and, in the area of the pivot joint of the distal end portion of the shank, via a connection lever. The distal end portion of the second transmission element can correspondingly be connected to a proximal portion of the second transmission element via a rotatable intermediate piece and, in the area of the pivot joint, via a connection lever. The connection levers can in particular be arranged in a radial outer area of the shank. The rotatable shaft for controlling the rotation movement of the tool preferably extends in the interior of the shank, in particular approximately coaxially with respect to a respective longitudinal axis both of the proximal portion of the shank and also of the distal end portion. The pivot joint for pivoting the distal end portion of the shank, including the rotatable shaft and the first transmission element in the area of the pivot joint, can be designed in the manner described in the as yet unpublished patent applications DE 102015015664.0 and DE 102015015655.1, which are in this regard incorporated by reference into the present application. In this way, a particularly versatile medical instrument is created in which the at least one movable jaw part can be locked in particular a holding position for immobilizing a grasped object, without substantial loading of the rotary bearings and of the proximal portions of the first and the second transmission element.

According to a particularly preferred embodiment of the invention, the at least one locking element is pre-tensioned into a locking position by a spring force. For example, in the case where the interspace between the mutually assigned oblique surfaces tapers in a wedge shape in the distal direction, this means that the locking element is spring-loaded in the distal direction. This has the effect that, when no axial force is exerted via the second transmission element, the locking element is pressed into the locking position and, consequently, the at least one movable tool element is locked. For unlocking, the at least one locking element is moved counter to the spring force by means of the second transmission element, in particular pulled out from the interspace, tapering in a wedge shape, to such an extent that the contact with at least one of the oblique surfaces is canceled. The safety of use of the medical instrument can be increased in this way, since accidental release of the movement of the at least one movable tool element can be avoided with greater certainty.

Preferably, a control spring, with which the at least one locking element is spring-loaded, is arranged in a handle of the medical instrument. The cleaning and sterilizing of the medical instrument is thus made easier, since the handle is not generally in direct contact with body fluids. The force exerted by the control spring and transmitted via the second transmission element is relatively small, and therefore the transmission of this force via the second transmission element does not lead to substantial loading of the rotary bearings.

It will be appreciated that the aforementioned features and the features still to be explained below can be used not only in the respectively cited combination but also in other combinations or singly, without departing from the scope of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 4 shows the medical instrument according to FIGS. 1a and 1b in an overall view.

DETAILED DESCRIPTION

Figure 1A:
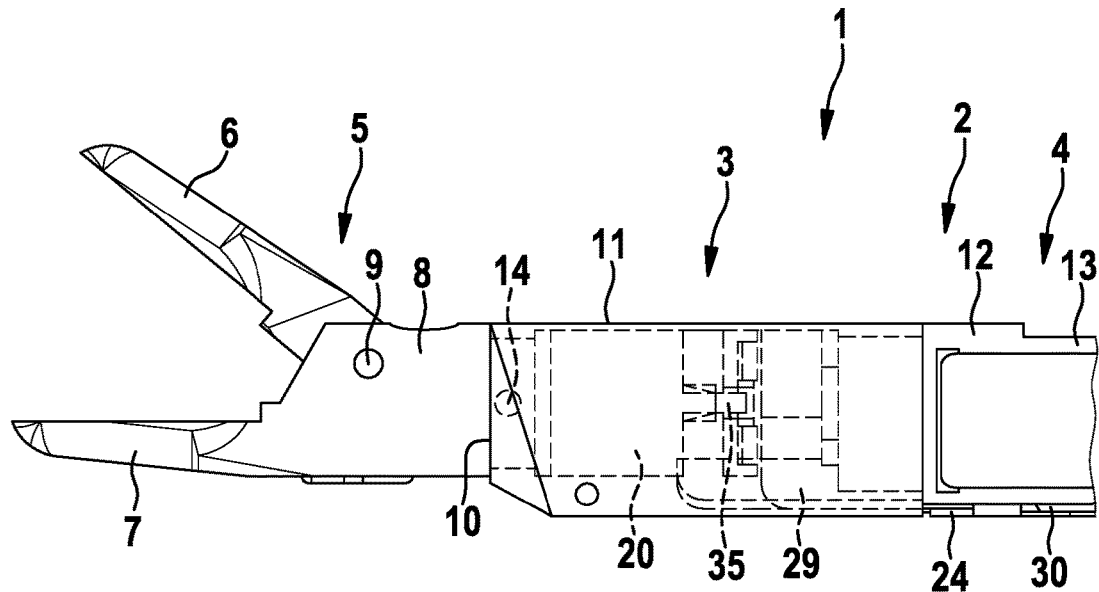
FIGS. 1a and 1b show the distal end area of a medical instrument according to an illustrative embodiment of the invention with opened jaw parts in a partially transparent side view (FIG. 1a) and in an axial sectional view (FIG. 1b)

An illustrative embodiment of a medical instrument according to the invention is shown in FIG. 1a in a partially sectioned view in which only a distal end area is depicted. The medical instrument 1 comprises an elongate shank 2 which is suitable for insertion into a cavity of a human or animal body and which comprises a distal end portion 3 and a proximal portion 4, of which proximal portion 4 of the shank only the distal end is shown in FIG. 1a. The medical instrument 1 further comprises a tool 5, which is arranged on the distal end of the distal end portion 3 of the shank 2. The tool 5 comprises two jaw parts 6, 7, of which a first jaw part 6 is mounted pivotably on a main part 8 of the tool 5, and a second jaw part 7 is connected rigidly to the main part 8. In the illustrative embodiment shown, the jaw parts 6, 7 are designed for grasping and holding a surgical needle. Parallel furrows, for example, can be arranged on the inner sides of the jaw parts 6, 7 in order to securely hold a surgical needle. The pivot axis 9 of the pivotable jaw part 6 extends transversely with respect to a longitudinal axis of the distal end portion 3 of the shank 2. The main part 8 is mounted, with a rotary bearing 10, so as to be rotatable about the longitudinal axis of the distal end portion 3 relative to an outer tube 11 of the distal end portion 3 of the shank 2. At the proximal end, the outer tube 11 is connected fixedly to a joint part 12, which is mounted on the distal end area of an outer tube 13 of the proximal portion 4 of the shank 2 so as to be pivotable about a transverse axis. In FIG. 1a, the pivot axis about which the distal end portion 3 is pivotable with respect to the proximal portion 4 of the shank 2 is perpendicular to the drawing plane.

Figure 1B:
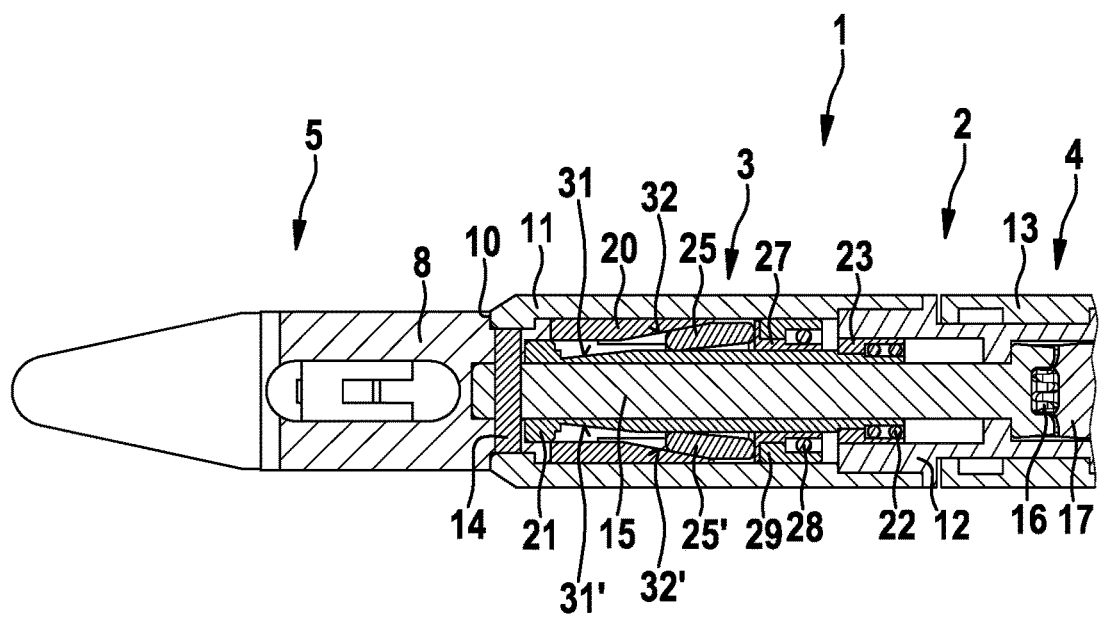

FIG. 1b shows the distal end area of the medical instrument 1 in an axial longitudinal section, the sectional plane in FIG. 1a being perpendicular to the drawing plane. As is shown in FIG. 1b, the main part 8 is connected by a pin 14 to a distal end portion 15 of a rotatable shaft for conjoint rotation therewith. At its proximal end, the distal end portion 15 of the rotatable shaft is connected by a toothing 16 to a proximal portion 17 of the rotatable shaft, which proximal portion 17 extends within the proximal portion 4 of the shank 2 and permits a rotation of the main part 8 and therefore of the jaw parts 6, 7 about the longitudinal axis of the distal end portion 3 of the shank 2.

A guide sleeve 20 is arranged inside the outer tube 11 of the distal end portion 3 of the shank 2 and is fixedly connected to the main part 8. The function of the guide sleeve 20 is described in more detail below. A tensioning sleeve 21, which receives the distal end portion 15 of the rotatable shaft and slides thereon, is mounted inside the guide sleeve 20 so as to be displaceable in the longitudinal direction but rotationally fixed with respect to the main part 8 and with respect to the guide sleeve 20. At the distal end, the tensioning sleeve 21 is coupled to the pivotable jaw part 6 in such a way that an axial displacement of the tensioning sleeve 21 in the distal direction causes the jaw part 6 to open, and an axial displacement in the proximal direction causes the jaw part 6 to close. At the proximal end, the tensioning sleeve 21 is connected, via a rotary bearing 22, to a likewise axially displaceable intermediate piece 23, which in turn is connected via a connection lever 24 to a pull rod extending on or in the proximal portion 4 of the shank 2 (see FIG. 1a). The pull rod, the connection lever 24, the intermediate piece 23, the rotary joint 22 and the tensioning sleeve 21 form a first transmission element, the axial displacement of which allows the movement of the movable jaw part 6, for opening and closing the forceps mouth formed by the jaw parts 6, 7, to be controlled from the direction of the proximal end of the shank 2.

Two locking elements 25, 25' arranged symmetrically with respect to the longitudinal axis are guided longitudinally displaceably in the guide sleeve 20. The locking elements 25, 25' are connected to an annular locking carriage 27 mounted longitudinally displaceably on the tensioning sleeve 21. The locking carriage 27 is connected rotatably, via a rotary bearing 28, to an intermediate piece 29, which is connected by a connection lever 30 to a push rod, which extends on or in the proximal portion 4 of the shank 2 (see FIG. 1a). Together with the connection lever 30, the intermediate piece 29, the rotary bearing 28 and the locking carriage 27, this push rod constitutes a second transmission element, by which an axial displacement of the locking elements 25, 25' can be brought about from the direction of the proximal end of the shank 2.

As can be seen in FIG. 1b, the tensioning sleeve 21 has, on its outer side, two oblique surfaces 31, 31', which each rise radially in the proximal direction, i.e. the distance from the longitudinal axis of the tensioning sleeve 21 or of the distal end portion 3 of the shank 2 increases in the proximal direction. On its inner side, the guide sleeve 20 has two mating surfaces 32, 32' which are each arranged opposite the surfaces 31, 31'. The mating surfaces 32, 32' likewise rise in the proximal direction. The angle of inclination of the mating surfaces 32, 32' to the longitudinal axis is greater than the angle of inclination of the oblique surfaces 31, 31'. In the position of the tensioning sleeve 21 shown in FIGS. 1a and 1b, i.e. with the jaw parts 6, 7 opened, the oblique surfaces 31, 31' and the mating surfaces 32, 32' are mutually offset in the axial direction, such that the locking elements 25, 25' cannot be pushed between the mutually assigned oblique surfaces. The movable jaw part 6 can thus be freely pivoted by displacement of the first transmission element.

Figure 2A:
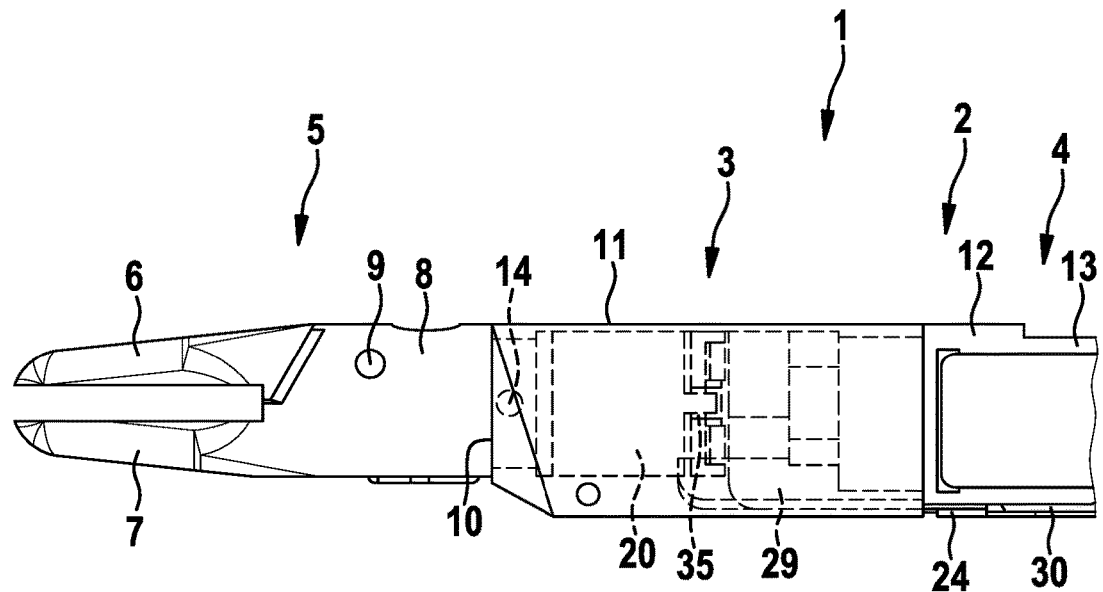
FIGS. 2a and 2b show the distal end area of the medical instrument according to FIGS. 1a and 1b in corresponding views, but with closed jaw parts.
Figure 2B:
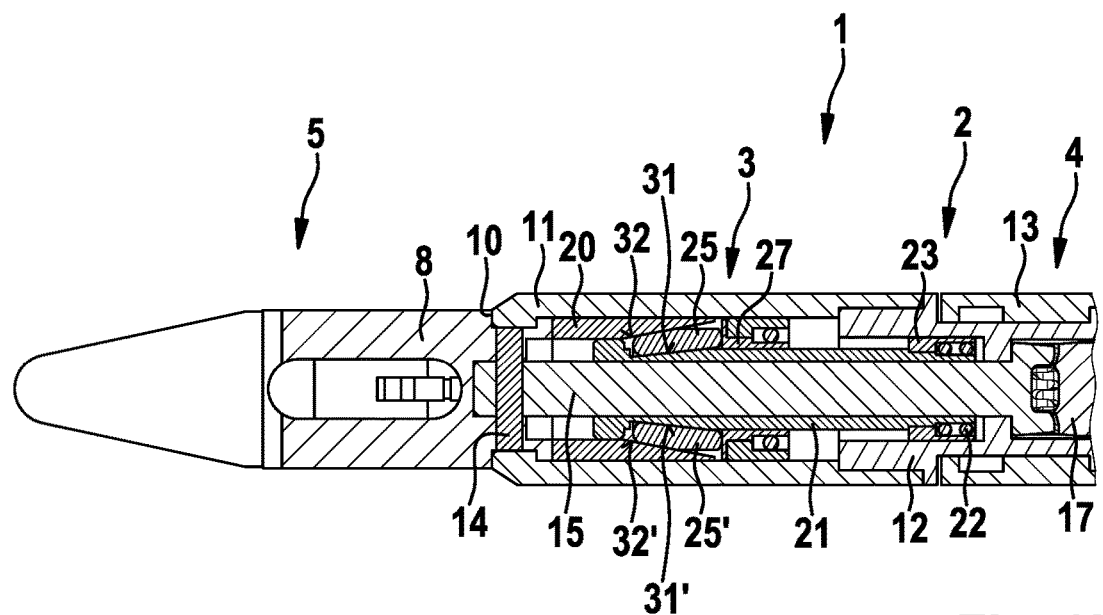

In FIGS. 2a and 2b, the distal area of the medical instrument 1 is shown as in FIGS. 1a and 1b, but the forceps mouth is closed in FIGS. 2a and 2b. In the closed position shown in FIGS. 2a and 2b, it is possible, for example, for a surgical needle (not shown) to be held between the jaw parts 6, 7. As can be seen in particular in FIG. 2b, the tensioning sleeve 21 is displaced in the proximal direction in relation to the position when the jaw part 6 is opened (see FIGS. 1a and 1b). For this purpose, the pull rod extending in or on the proximal portion 4 of the shank 2 has been pulled in the proximal direction, as a result of which the tensioning sleeve 21 has been displaced via the connection lever 24, the intermediate piece 23 and the rotary bearing 22. On account of the displacement of the tensioning sleeve 21, the oblique surfaces 31, 31' are now each arranged lying opposite the oblique mating surfaces 32, 32' in such a way that a greater interspace is formed between these. Since the angle of inclination of the mating surfaces 32, 32' is greater than that of the oblique surfaces 31, 31', the interspace has a wedge-shaped configuration in the axial longitudinal section shown in FIG. 2b. In the position of the tensioning sleeve 21 as shown in FIG. 2b, the interspaces are wide enough to receive a respective locking element 25, 25'. As can be seen from a comparison with FIG. 1b, the locking carriage 27 according to FIG. 2b has for this purpose been displaced in the distal direction. This can be brought about by suitable actuation of the push rod extending in or on the proximal portion 4 of the shank 2, which push rod controls a corresponding axial displacement of the locking carriage 27 via the connection lever 30, the intermediate piece 29 and the rotary bearing 28. The locking carriage 27 in turn displaces the locking elements 25, 25' in the distal direction. The force for displacing the push rod in the distal direction and for moving the locking elements 25, 25' into the interspaces is applied by a control spring arranged in a handle of the instrument (see FIG. 4).

The locking elements 25, 25' have a wedge shape at least in their distal area, wherein the wedge angle approximately corresponds to the opening angle of the interspace formed between the oblique surfaces 31, 31' and the respective mating surfaces 32, 32'. As is shown in FIG. 2b, the locking elements 25, 25' can be displaced in the distal direction until they bear on the respective oblique surface 31, 31' of the tensioning sleeve 21 and at the same time on the respective mating surface 32, 32' of the guide sleeve 20; a distal limit stop for the movement of the locking elements 25, 25' is thereby reached. The locking elements 25, 25' are connected movably to the locking carriage 27 in such a way that, when pushed into the interspaces, they are able to follow the oblique surfaces 31, 31' and the mating surfaces 32, 32' until they bear on both sides. In this state, an axial displacement of the tensioning sleeve 21 in the distal direction is no longer possible, since it is blocked by the locking elements 25, 25'. The angles of inclination of the oblique surfaces 31, 31' and of the mating surfaces 32, 32' are chosen in such a way that there is a self-retaining effect, wherein a displacement of the tensioning sleeve 21 in the proximal direction is also prevented. For this purpose, the oblique surfaces 31, 31' are inclined by approximately 5° to 6° with respect to the direction of displacement of the tensioning sleeve 21, which is oriented parallel to the longitudinal axis of the distal end portion 3 of the shank 2, and the mating surfaces 32, 32' are inclined by approximately 10° to 12° with respect to the longitudinal axis. The movable jaw part 6 is thus locked in a self-retaining manner, and a surgical needle held between the jaw parts 6, 7 is held fixedly, without a user having to exert more force for this purpose. The locking elements 25, 25', like the tensioning sleeve 21 and the guide sleeve 20, are made of stainless steel, for example, and the locking elements 25, 25' and also the surfaces 31, 31' and the mating surfaces 32, 32' are preferably hardened.

In order to hold a surgical needle, the latter is initially grasped by closure of the jaw part 6. In doing this, the locking elements 25, 25' are located outside the interspaces between the surfaces 31, 31' of the tensioning sleeve 21 and the mating surfaces 32, 32' of the guide sleeve 20. The first transmission element is pulled in the proximal direction in order to close the forceps mouth, while the second transmission element remains in its proximal end position (see FIGS. 1a and 1b). During closure of the forceps mouth, the interspaces formed between the surfaces 31, 31' and the mating surfaces 32, 32' increase in size. When the needle has been grasped between the jaw parts 6, 7, and when the jaw parts 6, 7 are thus located in their closed position, a holding force is exerted on the movable jaw part 6 via the first transmission element, in order to hold the needle sufficiently securely. Thereafter, by means of a displacement of the second transmission element in the distal direction, the locking elements 25, 25' are pushed into the interspaces, which are formed between the surfaces 31, 31' and the mating surfaces 32, 32' and which are sufficiently wide in this position of the tensioning sleeve 21, as far as the distal limit stop (see FIGS. 2a and 2b). If the first transmission element is now let go at the proximal end, the locking elements 25, 25' jam and block a displacement of the tensioning sleeve 21 relative to the guide sleeve 20. In this way, the movable jaw part 6 is locked in its position, and the tensioning sleeve 21 remains tensioned and exerts the holding force on the jaw part 6.

Since the rotary bearing 10 of the tool is unloaded, the jaw parts can be easily rotated by application of a torsional force via the rotatable shaft 15, 17. The rotary bearings 22, 28 of the first and second transmission element, respectively, are also unloaded and do not impede the rotation. Moreover, the distal end portion 3 of the shank 2 can be freely pivoted with respect to the proximal portion 4 of the shank 2.

To release the locking, the tensioning sleeve 21 is again subjected to tensile force via the first transmission element. The clamping force is thereby taken from the locking elements 25, 25' which, from the direction of the handle, can now be pulled out of the interspaces in a controlled manner via the second transmission element. With the locking elements 25, 25' pulled back, the tensioning sleeve 21 can move freely again, the jaw part 6 can be opened by means of the first transmission element, and the needle can be released from the jaw parts 6, 7.

Figure 3:
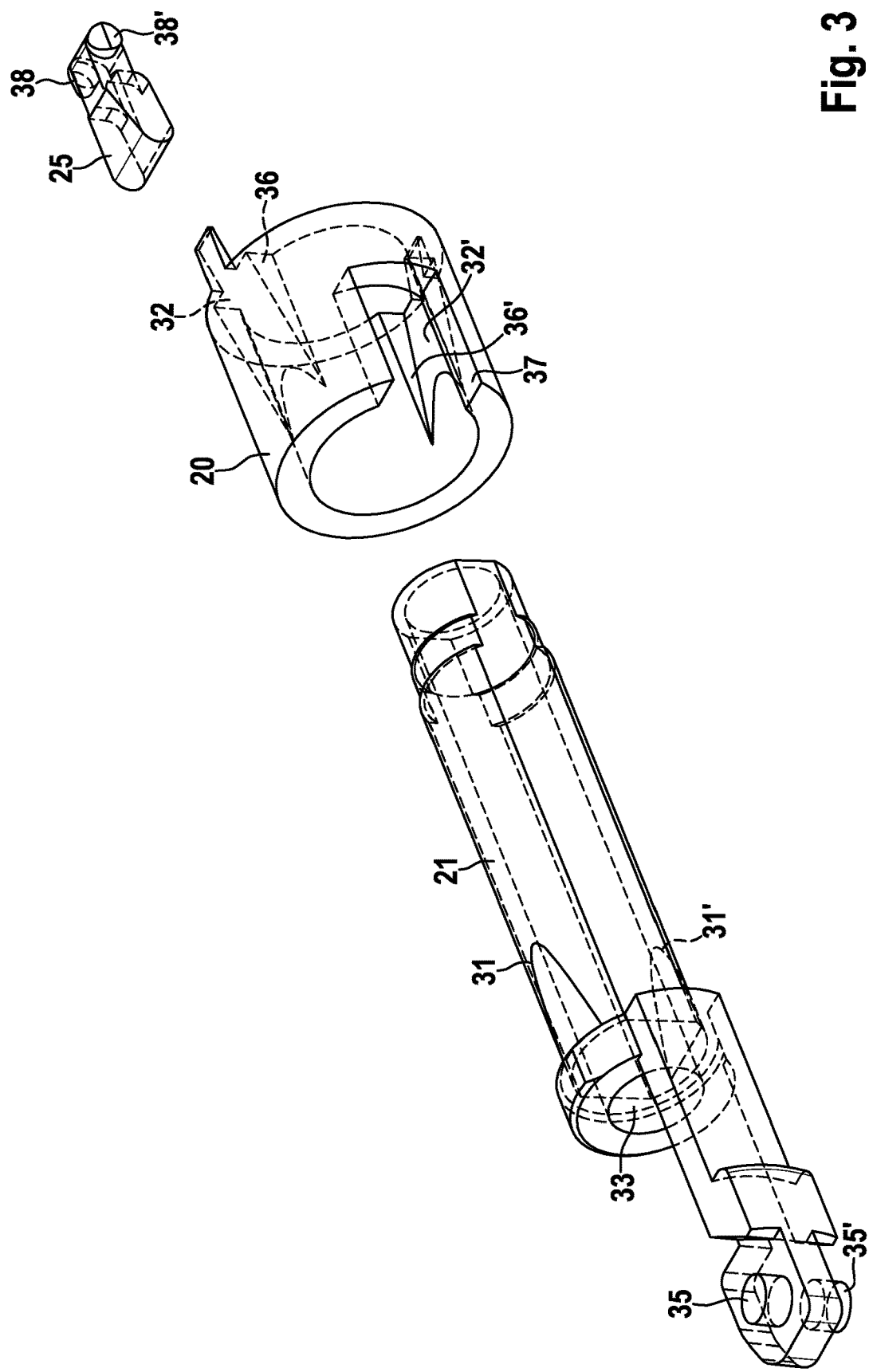
FIG. 3 shows a tensioning sleeve, a guide sleeve and a locking element of the medical instrument according to FIGS. 1a and 1b.

FIG. 3 shows the tensioning sleeve 21, the guide sleeve 20 and a locking element 25 in an exploded view. As is shown in FIG. 3, the tensioning sleeve 21 is substantially cylindrical and has a continuous inner cavity 33 for receiving the distal end portion 15 of the rotatable shaft (see FIG. 1b). Moreover, the tensioning sleeve 21 has a distal extension piece 34 which carries pins 35, 35', the latter engaging in recesses of a fork-shaped extension piece of the pivotable jaw part 6 in order to pivot the jaw part 6 by axial displacement of the tensioning sleeve 21. Two plane and oblique surfaces 31, 31' are arranged on opposite faces on the outer side of the tensioning sleeve 21.

The guide sleeve 20 is designed substantially as a cylindrical tube which, on its inner side, has two opposite grooves 36, 36' in which the locking elements 25, 25' are guided. The respective bottom of the grooves 36, 36' forms the oblique mating surfaces 32, 32'. These are each plane surfaces in the illustrative embodiment shown. In the medical instrument 1, the tensioning sleeve 21 is received in a longitudinally displaceable manner inside the guide sleeve 20, and, on account of the engagement of the extension piece 34 in the recess 37 of the guide sleeve 20, the tensioning sleeve 21 is connected to the guide sleeve 20 for conjoint rotation therewith and, when the main part 8 is rotated via the distal portion 15 of the rotatable shaft and via the pin 14, the tensioning sleeve 21 is entrained in rotation by the main part 8. The oblique surfaces 31, 31' on the outer side of the tensioning sleeve 21 are arranged opposite the grooves 36, 36' and therefore opposite the mating surfaces 32, 32'.

The locking element 25 is received with its distal part in the groove 36 and is guided in the longitudinal direction in said groove 36. The distal part of the locking element 25 has a wedge-shaped configuration, such that the locking element 25 can be easily inserted into the groove 36 until it makes surface contact with the surface 31 and the mating surface 32. At the proximal end, the locking element carries two lateral lugs 38, 38', with which it is articulated on the locking carriage 27 (see FIG. 1b). The locking element 25 can thus be displaced in the axial direction by means of the locking carriage 27 and is pivotable about the axis formed by the lugs 38, 38'. The locking element 25 is thus sufficiently movable in the radial direction in order to enter the interspace formed between the surface 31 and the mating surface 32, as far as the limit stop defined by bearing on the surface 31 and the mating surface 32. The second locking element 25', arranged axially opposite the locking element 25, is configured in the same way and guided in the groove 36'.

FIG. 4 shows an overall view of the medical instrument according to the described illustrative embodiment. As is shown in FIG. 4, the distal end portion 3 of the shank 2 can be pivoted with respect to the proximal portion 4 of the shank 2. According to FIG. 4, a handle 40 is arranged at the proximal end of the shank 2 and has a grip with two grip parts 41, 41' which are connected to the proximal end of the pull rod 46 of the first transmission element. When the grip parts 41, 41' are pressed together, the pull rod 46 can be displaced in the proximal direction and, in this way, the movable jaw part 6 can be moved toward the stationary jaw part 7 in order, for example, to grasp a surgical needle. A slide 42, which is connected to the push rod of the second transmission element, is arranged on a grip part 41. When the needle has been firmly grasped, the movable jaw part 6 can be unlocked by displacement of the slide 42 in the distal direction. In addition, a catch 43 is provided between the grip parts 41, 41'. Moreover, the handle 40 has a rotary wheel 44 with which the forceps mouth can be rotated about a longitudinal axis and which for this purpose is connected to the proximal portion 17 of the rotatable shaft, and also a further rotary wheel 45 with which the pivoting movement of the distal end portion 3 of the shank 2 can be controlled.

For the sake of clarity, not all the reference signs are shown in all of the figures. Reference signs not explained in connection with one figure have the same meaning as in the other figures.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A medical instrument with an elongate shank, and a tool which is arranged on a distal end portion of the shank and which comprises two tool elements interacting with each other, for the purpose of holding an object, of which at least one tool element is movable by a longitudinally displaceable first transmission element, wherein a distal end portion of the first transmission element has a surface inclined with respect to a direction of displacement, and the distal end portion of the shank, or an element connected non-displaceably thereto, has a mating surface which is inclined with respect to the direction of displacement and which, with the inclined surface, forms an interspace dependent on a displacement of the distal end portion of the first transmission element, and in that at least one locking element is present, which is movable into the interspace in order to block the displacement of the first transmission element and is movable out of said interspace in order to release the blocking.

2. The medical instrument according to claim 1, wherein the inclined surface is arranged on an outer side of the distal end portion of the first transmission element, and the mating surface is arranged on an inner side of a tubular element.

3. The medical instrument according to claim 1, wherein the tool elements interacting with each other can be closed by a displacement of the first transmission element in a proximal direction, and in that the inclined surface and the mating surface rise radially in the proximal direction.

4. The medical instrument according to claim 1, wherein the interspace is wedge-shaped.

5. The medical instrument according to claim 1, wherein the inclined surface and the mating surface are inclined at such an angle with respect to the direction of displacement that the displacement of the first transmission element can be blocked in a self-retaining manner.

6. The medical instrument according to claim 1, wherein the at least one locking element is wedge-shaped.

7. The medical instrument according to claim 1, wherein the at least one locking element is connected radially movably to a distal end portion of a second transmission element.

8. The medical instrument according to claim 7, wherein the at least one locking element is articulated with two lugs on the distal end portion of the second transmission element.

9. The medical instrument according to claim 1, wherein the at least one locking element is guided displaceably in a groove of the distal end portion of the shank, and a bottom of the groove forms the mating surface.

10. The medical instrument according to claim 1, wherein two locking elements are present, which are movable jointly.

11. The medical instrument according to claim 1, wherein the tool is rotatable about a rotation axis parallel to a longitudinal axis of the distal end portion of the shank, and the distal end portion of the first transmission element is mounted rotatably about the rotation axis relative to a proximal portion.

12. The medical instrument according to claim 1, wherein the distal end portion of the shank is pivotable about a transverse axis relative to a proximal portion of the shank.

13. The medical instrument according to claim 1, wherein the at least one locking element is spring-loaded into a locking position.

14. The medical instrument according to claim 13, wherein a control spring for spring-loading the at least one locking element is arranged in a handle of the medical instrument.

* * * * *